United States Patent [19]
Borodulin et al.

[11] Patent Number: 4,748,971
[45] Date of Patent: Jun. 7, 1988

[54] VIBRATIONAL APPARATUS FOR ACCELERATING PASSAGE OF STONES FROM URETER

[76] Inventors: German Borodulin, 2518 Clement St., #4, San Francisco, Calif. 94121; Alexander Shkolnik, 962 S. El Camino Real, #202, San Mateo, Calif. 94402-2301; Maxim Persidsky, 35 Temescal Ter., San Francisco, Calif. 94118; Joachim W. Thüroff, 2119 30th Ave., San Francisco, Calif. 94116

[21] Appl. No.: 8,660

[22] Filed: Jan. 30, 1987

[51] Int. Cl.⁴ ............................................. A61B 17/22
[52] U.S. Cl. .................................. 128/24 A; 128/328; 128/24 R
[58] Field of Search ..................... 128/328, 24 A, 24 R

[56] References Cited

U.S. PATENT DOCUMENTS

| | | | |
|---|---|---|---|
| 2,990,616 | 7/1961 | Balamuth et al. | 128/24 A X |
| 3,792,701 | 2/1974 | Kloz et al. | 128/328 |
| 3,823,717 | 7/1974 | Pohlman et al. | 128/328 X |
| 3,927,675 | 12/1975 | Pohlman et al. | 128/328 |

Primary Examiner—Michael H. Thaler
Attorney, Agent, or Firm—David Pressman

[57] ABSTRACT

A vibrational method and apparatus for accelerating and increase in efficiency of passage of stones from the ureter comprises introducing into the ureter (U) of a catheter (10) with a vibrating head (12) which imparts radial oscillations to the walls of the ureter at a distance of 0 to 30 mm from the areas where the stone (S) is lodged. Catheter (10) is a flexible tube which has a head (12) which is expandable radially and axially by means of an oscillating element (24) driven from a reciprocating vibrational drive (26). Drive (26) has a tapering end (32) which, during its reciprocations, causes expansions and constrictions of the resilient head, due to its interaction with inner projections (18) and (20). The apparatus is universal in its application and can be used without any changes for pushing the stone, located in the upper part of the ureter, back to the kidney, where the stone can be more readily disintegrated by means of subsequent extracorporeal shock wave lithotripsy. By replacing some parts, the apparatus can be converted into an ultrasonic device for accelerating passage of stones or into an ultrasonic device for destruction of stones in the ureter.

5 Claims, 2 Drawing Sheets

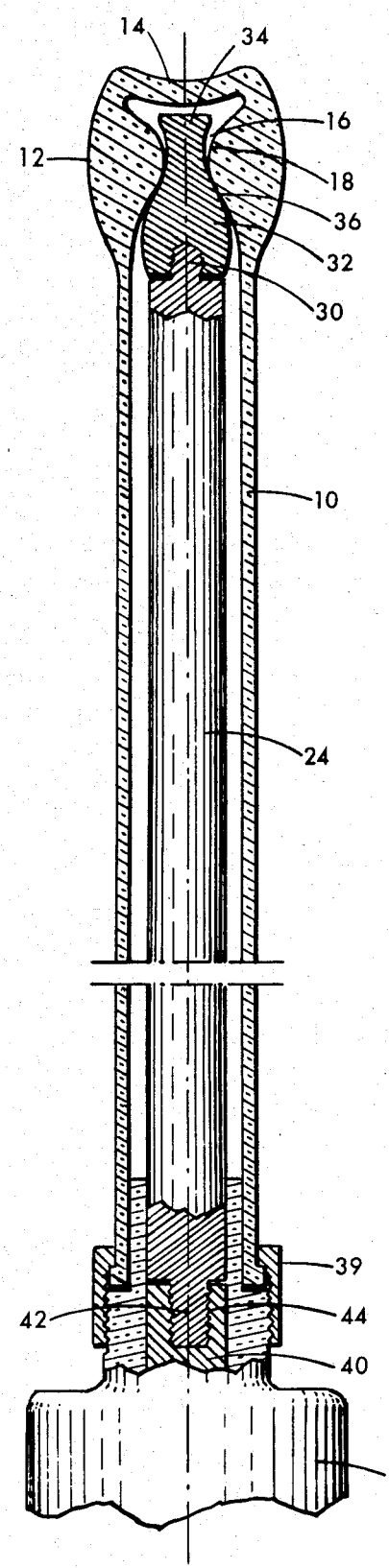
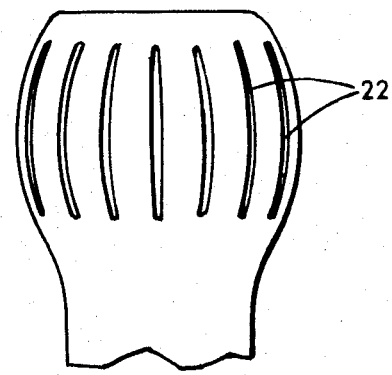
Fig. 3
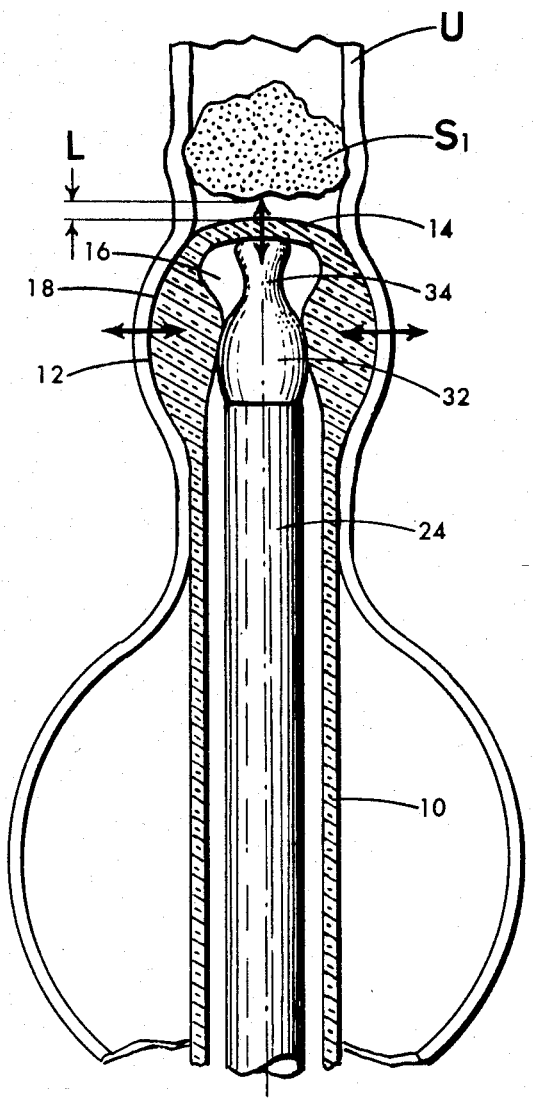
Fig. 2
Fig. 1

VIBRATIONAL APPARATUS FOR ACCELERATING PASSAGE OF STONES FROM URETER

BACKGROUND—FIELD OF THE INVENTION

The present invention relates to the field of urology, particularly to a method and apparatus for acceleraton and more efficient spontaneous removal of stones from the ureter.

BACKGROUND—DESCRIPTION OF THE PROBLEM

Urolithiasis, the presence of urinary stones, is a widespread urological disease. Medical statistics indicate It is well known that the average number of hospital admissions for removal of urinary stones is about 1 per 1000 of population per year. A considerable percentage of patients have urolithiasis due to ureteral stones (those which originate in the renal collecting system and pass into the ureter). Ureteral stones frequently become lodged in place, causing and cause inflammation and other symptoms.

The known methods of treating urolithiasis can be roughly divided into operative and non-operative treatments. Since operative treatments tend result in more complications, they are used only in cases where there are no alternatives. Non-operative treatments include manipulative treatment and expectant therapy. Manipulative treatment consists of the use of various baskets (snares), loops, and catheters for the forcible removal of stones fro the urinary tract. Expectant therapy consists of hydration (i.e., increase intake of water to cause the body to form more urine) by the body for formation of an increased amount of urine) and the liberal use of the analgesics and spasmolytics (i.e., agents that relieve or prevent convulsions or spasmodic pains). Also stones can be destroyed by means of ultrasonic methods or electrohydraulic methods (in which the stones are destroyed by shock waves generated in liquid under the effect of electric discharges), or with the use of extracorporeal shock wave lithotripsy (which is an inoperative method destroying stones in the kidney by the ultrasonic energy of shock waves generated from outside the patient's body).

The non-operative methods of stone removal involve a risk of complications, such as urinary track infections, hematuria (the discharge of urine containing blood), urethral perforation, and even complete avulsion (forcible tearing) of the ureter. In some cases, breakage and entrapment of the stone basket or snare can take place, requiring surgical intervention. In the case of stone description, small fragments of the stones can be impacted in the urinary tract and can be then removed only by surgical intervention. Nevertheless, statistics show that stones having diameters less than 4 mm which are located in the distal ureter (far from the kidney) pass spontaneously in 90% of cases; that stones having diameters between 4 and 5.9 mm pass spontaneously in only 50% of cases, whereas those having diameters greater than 6 mm pass in only 20% of cases without surgical intervention. Stones located in the proximal ureter, i.e., close to the kidney are much less likely to pass spontaneously, and stones larger than 8 mm in diameter usually require surgical intervention.

While spontaneous passage, if possible, is the most desirable method of removing a stone from the ureter, spontaneous passage of a stone may require a long time, or a sonte may never pass at all.

The presence of a ureteral stone prevents normal urethral peristalsis (i.e. periodic contraction waves of the ureteral walls which force the urine from the ureter towards the urethra), and causes spasms and inflammation processes of the ureter in the area of the stone. This condition, if not corrected, can cause formation of urethral strictures, kidney disfunction, and pyelonephritis (i.e., a diseases caused by bacterial or other infections of the pelvis of the kidney). The longer the stone remains in the ureter, the greater the chances of the above complications.

When a stone is located in the proximal ureter, it is advantageous to push it back into the kidney by means of a catheter. When in the kidney, the stone can be more easily destroyed by means of extracorporeal shock wave lithotripsy. However, existing procedures for pushing stones back into the kidney use catheters and are not very efficient, especially when the stone is impacted (lodged and retained) in the ureter.

Thus persons with ureteral stones would greatly benefit from any improved method for removal of ureteral stones, as well as from a more efficient and reliable method of pushing such stones from the upper part of the ureter back into the renal system for subsequent destruction by extracorporeal lithotripsy.

OBJECTS AND ADVANTAGES OF THE PRESENT INVENTION

Therefore one object of the present invention is to provide an efficient method and apparatus for accelerating the spontaneous passage of stones from the ureter. Another object is to provide a universal apparatus which can also be used for pushing such stones back into the kidney for subsequent destruction by extracorporeal lithotripsy. The invention also is aimed at providing an apparatus which, in addition to the two above-mentioned functions, can be quickly converted into the apparatus for ultrasonic destruction of stones. Further object is to provide an apparatus which is simple in construction, easy to use, and inexpensive to manufacture. Other objects, features, and advantages of the invention will be understood after consideration of the ensuing description and the attached drawings.

DRAWINGS

FIG. 1 is a longitudinal sectional view of apparatus according to the invention.

FIG. 2 is a schematic longitudinal sectional view showing the position of the apparatus of FIG. 1 during operation.

FIG. 3 is an external view of an expandable head of the apparatus of FIG. 1.

Figure 5:
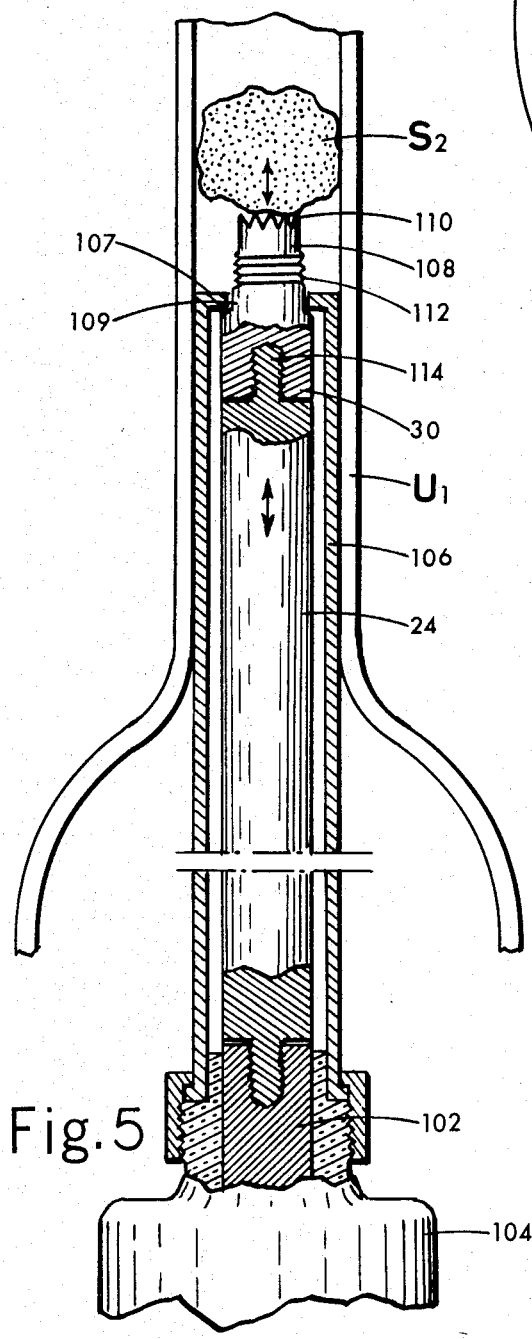
FIG. 5 is a partial longitudinal sectional view of the apparatus in a form suitable for ultrasonic destruction of stones.

Reference Numerals Used in the Specification and Drawings

10—catheter
12—head
14—end face

16—cavity
18—inner circular projection
22—longitudinal slits
24—core element
26—mechanical vibrator
30—threaded portion
32—replaceable cap
34—cylindrical tip
36—tapering surface
39—nut
40—oscillating element
42—thread
44—threaded hole
102—oscillating element
104—ultrasonic transducer
106—catheter
107—end of the catheter
108—cutter
109—through opening
110—cutting teeth
112—thread
114—tail part of the cutter
116—dome-like head
118—plastic coating
U—ureter
$S_1$, $S_2$—stones
K—kidney
L—distance from the catheter head to a stone FIGS. 1 to 3—Description of the Method and Apparatus for Accelerating Passage of Stones from the Ureter According to the invention, we have discovered a method of accelerating passage of stones. This method is based on our finding that a short-term application of oscillations to the walls of the ureter below the stone activates peristalsis of the ureter over its whole length. This accelerates the natural passage of stones from the ureter and increases the percentage of stones which pass from the ureter.

FIGS. 1 to 4 show the apparatus of the invention in a form suitable for both transmission of mechanical oscillations to the walls of the ureter and pushing the stone back into the kidney.

The apparatus consists of a flexible tubular catheter 10 which, as a conventional catheter, is made of a thin plastic tube having a diameter of about 3 mm and a wall thickness of about 0.3 mm. Catheter 10 has a head 12 at its distal end of a slightly increased diameter as compared to the diameter of the tubular portion of the catheter. Head 12 has a substantially spherical shape with a concave end face 14 which is flat at its center. The head can be made integral with the tubular part of the catheter and is formed of the same resilient plastic material. If necessary, however, it can be made of a softer material than the tubular part of the catheter and can be attached to it, e.g., by thermal fusion. The diameter of head 12 is approximately 3.5 mm.

The interior of head 12 has a cavity 16 which is bordered by the inner side of end face 14 and an inwardly bulging continuous circular projection 18 formed on the inner walls of head 12. As a result, cavity 16 has, in longitudinal cross section, a configuration in the form of two opposite cones facing each other. Head 12 also has longitudinal slits 22 which are shown in FIG. 3. The slits can be cut all through the wall of the head or just part of the wall thickness. The slits reduce its resistance to radial expansion.

Catheter 10 contains a core element 24 which may comprise a wire and can serve as coupling element for transmission of mechanical oscillations from a conventional mechanical vibrator 26 (FIG. 1), or as a waveguide for transmission of ultrasonic waves from a transducer 104 (FIG. 5) which will be described later in connection with ultrasonic application of the apparatus. Core element 24 may have a length of about 30 cm. Mechanical vibrator 26 may have frequencies adjustable in a range of 0 to 200 Hz and amplitudes of vibrations from 0 to several millimeters.

The distal end of core element 24 has a threaded portion 30 of a reduced diameter. A replaceable tapering cap 32 with a cylindrical tip 34 is screwed onto porti 30 of core element 24. In an assembled state, cylindrical tip 34 is inserted into the conical part of cavity 16 so that the tip can contact the back side of concave end face 14. Tapering surface 36 of cap 32 conforms to the shape of circular projection 18 inside head 12. Thus when core element 32 reciprocates, tapering surfaces 36 will contact circular projections 18, moving it radially outwardly, while tip 34 will push end wall 14 in an axial direction.

In the embodiment shown in FIGS. 1 to 4, the proximate end of catheter 10 is connected to the housing of vibrator 26, e.g., by a nut 39. Core element 24 is connected to an oscillating element 40 of the vibrator, e.g., by means of a thread 42 formed on the proximate end of the core which is engaged with a threaded hole 44 formed on the front end of the oscillating element.

Figure 4:
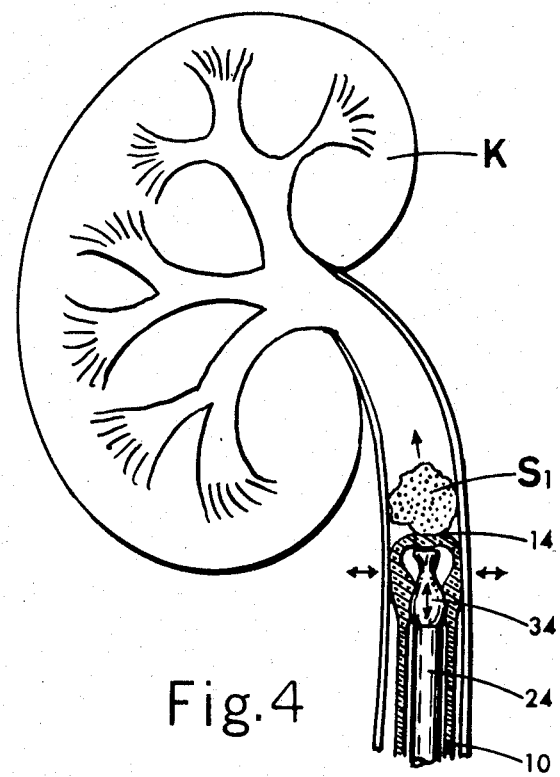
FIG. 4 is a longitudinal section view which illustrates application of the apparatus for pushing a stone back into the kidney.

FIGS. 2 and 4—Operation of Apparatus for Acceleration of the Passage of Stones from the Ureter or for Pushing the Stones Back Into the Kidney To accelerate the passage of stones from the ureter and to increase the percentage of stones which will pass spontaneously from the ureter, the apparatus of FIG. 1 is inserted into a ureter U (FIG. 2) in the same manner as a conventional catheter. It is inserted so that head 12 of the catheter is located slightly lower than a stone S which is has to be removed. Head 12 should be 0 to 20 mm from stone S.

Vibrator 26 is then energized so that its output element 40 reciprocates in the axial direction of the apparatus. The range of amplitudes and frequencies of the oscillations can be selected in a very wide range with frequencies from 0 to ultrasonic frequencies and with amplitudes from 0 to several millimeters.

The oscillations of output element 40 are transmitted to core element 24 which thereupon reciprocates. When core element 24 reciprocates, its cap 32 moves axially within the cavity of head 12 so that tapering surface 36 contacts circular projection 18 of head 12. This causes cap 12 to expand radially. The expansion is facilitated by slits 22 and by the action of tip 34, which acts against the inner side of wall 14. The directions of oscillations are shown in FIG. 2 by arrows.

The expansions of resilient head 12 are transmitted to the walls of the ureter beneath stone S where they improve peristaltic waves of the ureter, thereby reducing the spasm of the ureteral walls in the area where the stone is lodged. As a result, the spontaneous passage of the stone is accelerated.

This procedure can be used for removal, not only of a single stone, but for acceleration of passage of debris formed in the ureter after disintegration of the stone by a conventional electrohydraulic or ultrasonic methods. In the latter case, the principle of operation is the same as has been described above.

After completion of the procedure the apparatus is removed from the ureter, as with a conventional catheter.

When stone $S_1$ (FIG. 4) is located in the upper part of the ureter, it is advantageous to push it back into the kidney K where it can be easily destructed by means of extracorporeal lithotripsy. In this case catheter 10 is pushed further until it contacts stone $S_1$ prior to initiating the vibrations.

After vibrations or ultrasonic action is initiated, the catheter is slowly pushed forward. Flexible end wall 14 functions as a seat for the stone. Radial expansions of head 12, together with axial movement of wall 14 which is transmitted to the stone, facilitate movement of the stone back to the kidney and prevent the stone from impacting in the ureter. After completion of the procedure, the apparatus is removed from the ureter as with a conventional catheter.

FIG. 5—Apparatus of the Invention for Ultrasonic Destruction of Stones

FIG. 5 shows the apparatus of the invention in a form suitable for destruction of stones in the ureter by an ultrasonic method. For this purpose, core element 24, which in this case functions as a waveguide, is connected to an oscillating element or head 102 of an ultrasonic transducer 104. Core element 24 is inserted into a conventional tubular catheter 106, which in this case does not have an expandable head, but comprises a simple hollow tube with a closed end 107 having a through opening 109 for protrusion of a milling cutter 108. This cutter is substituted for cap 32 of the apparatus of FIG. 1 and has cutting teeth 110 on its end. The milling cutter is screwed onto threaded portion 30, which is in turn mounted on the distal end of core element 24. On its side surface, milling cutter 108 has a thread 112 used for a purpose described later. The diameter of cutting 108 and its threaded portion (about 1.8 mm) is smaller than the tail part 114 of the cutter so that the remaining part of end wall 107 of the catheter serves as a stopper for the cutter during its oscillations.

FIG. 5—Operation of the Ultrasonic Apparatus for Destruction of Stones within the Ureter For disintegration of stones in the ureter, the apparatus is used as a conventional ultrasonic stone disintegration instrument. Specifically, it is inserted into the ureter $U_1$ until its milling cutter 108 comes into contact with stone $S_2$. Then the physician energizes transducer 104. This causes ultrasonic vibrations to be transmitted to cutter 108 via waveguide 24. As a result, the vibrations from teeth 110 cause stone $S_2$ to fracture and break into many small pieces. After stone $S_2$ disintegrates, the apparatus is withdrawn from the ureter. Within a short after this procedure, the apparatus of FIG. 1 can be used to accelerate the spontaneous passage of stone debris formed in the ureter as a result of disintegration.

Figure 6:
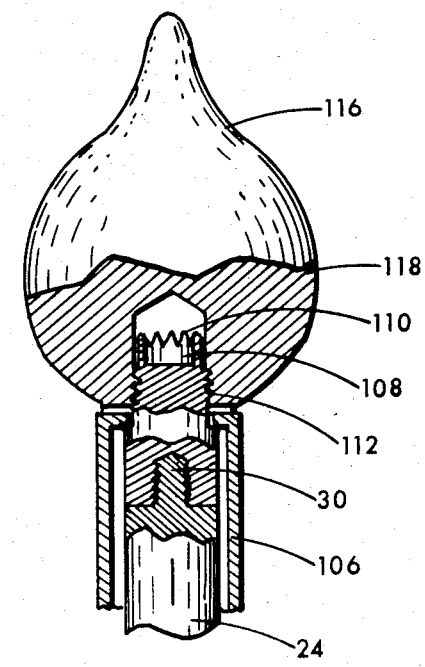
FIG. 6 is a longitudinal sectional view illustrating the apparatus of FIG. 1 in a position for transmission of ultrasonic waves to the walls of the ureter.

FIG. 6—Modification of the Apparatus for Transmission of Ultrasonic Oscillations to the Ureteral Walls FIG. 6 shows another modification of the apparatus of the invention which is suitable for application of ultrasonic oscillations to the walls of the ureter.

The apparatus of FIG. 5 can be converted without disassembly into the apparatus of FIG. 6 which can apply ultrasonic oscillations to the ureter's walls. The physician need thereby to screw a dome-like metal head 116 onto threaded part 112 (FIGS. 5 and 6) of milling cutter 108. Head 116 has a diameter slightly exceeding the diameter of catheter 106 and its surface is covered by a thin layer 118 of a plastic material suitable for medical application.

The apparatus of FIG. 6 is inserted into the ureter to a position a short distance from the stone (similar to the case of FIG. 2). The plastic-coated surface of dome-like head 116 will be in contact with the walls of the ureter. When the apparatus is energized, ultrasonic oscillations will be transmitted from transducer 104 through waveguide 24 to head 116 and thence to the walls of the ureter. This action will accelerate spontaneous passage of the stones or stone debris from the ureter.

CONCLUSION, RAMIFICATIONS, AND SCOPE

We have thus described and shown an efficient and simple method and apparatus for acceleration of spontaneous passage of stones from the ureter. The apparatus of the invention is universal in that it and can be used for various purposes from destruction of the stones to their pushing back into the kidney. The apparatus is simple to use and inexpensive to manufacture. It can employ a very wide range of frequencies and amplitudes of oscillations, from low frequencies to ultrasonic frequencies with amplitudes from several microns to several millimeters. The method and apparatus of the invention convert passive expectancy therapy into an active method of treatment.

The invention has been described and illustrated with reference to particular examples. The reader should not construe these examples as limiting the scope of the invention since many other ramifications are possible. For example, cap 32 may have a spherical, rather than conical shape. Different means can be used to connect the cap to the core element as well as the dome-like element to the cutter. The dome-like element can be connected directly to the core element and the conical cap can be used without cylindrical tip. It is also obvious that vibrations can be generated by sources other than a mechanical vibrator or an ultrasonic transducer. Thus, the scope of the invention should be determined not by examples given, but rather by the appended claims and their legal equivalents.

We claim:

1. A vibrational apparatus for accelerating the spontaneous passage of stones from the ureter, pushing such stones back from said ureter to the kidney, and destroying such stones in said ureter, comprising:
    an external source of vibrations having a non-vibrating housing means and an axially-vibrating inner element;
    a flexible tubular catheter extending in an axial direction and having one end rigidly attached to said housing means and having at its other, opposite end a radially-expandable head with a closed flexible end face which can be radially deformed in said axial direction of said catheter; and
    a rod-like vibration transmitting means inserted into said catheter, one end of said vibration transmitting means being connected to said vibrating inner element so that said vibration transmitting means undergoes axial oscillations, the other end of said vibration transmitting means having interchangeable head means removably attached thereto for converting said axial oscillations into radial expansions of said radially-expandable head and axial deformations of said flexible end face of said radially-expandable head.

2. The vibrational apparatus according to claim 1 wherein said interchangeable head means comprises a conical cap removably attached to the end of said vibration transmitting means adjacent said head, said head of said catheter having a circular inwardly-directed projection on its inner wall, said conical cap having on its end facing the inner side of said closed end of the catheter, a tip which can selectively contact said inner side and impart axial oscillations thereto, so that during said axial oscillations, said conical cap engages said circular projection, thereby causing radial expansions of said head.

3. The vibrational apparatus according to the claim 1 wherein said head of the catheter has slits for facilitating said radial expansions of said head.

4. The vibrational apparatus according to claim 1 wherein said end face of said catheter has a concave configuration.

5. A vibrational apparatus according to claim 1 wherein said rod-like vibration transmitting means in connected to said interchangeable head means by threads on said other end of said rod-like vibration transmitting means.

* * * * *

UNITED STATES PATENT AND TRADEMARK OFFICE
CERTIFICATE OF CORRECTION

PATENT NO. : 4,748,971

DATED : June 7, 1988

INVENTOR(S) : Borodulin et al.

It is certified that error appears in the above-identified patent and that said Letters Patent are hereby corrected as shown below:

Abstract: 1. 2, change "increase in" to --increasing--.

Col. 1, 1. 8, change "acceleraton" to --acceleration--.

1. 16, change "It" to --it--.

1. 23, delete "and cause".

1. 27, after "tend" insert --to--.

1. 33, changer "fro" to --from--.

1. 36, delete ")".

11. 43, change "inoperative" to --non-operative--

1. 44, after "method" insert --for--.

1. 54, change "description" to --destruction--.

1. 64, after "kidney" insert --,--.

Col. 2, 1. 2, change "sonte" to --stone--.

Col. 3, 1. 64, change "just" to --can just be--.

Col. 4, 1. 12, change "porti" to --portion--.

Col. 5, 1. 53, after "short" insert --time--.

1. 65, change "need thereby to" to --needs to--.

UNITED STATES PATENT AND TRADEMARK OFFICE
CERTIFICATE OF CORRECTION

PATENT NO. : 4,748,971

DATED : June 7, 1988

INVENTOR(S) : Borodulin et al.

It is certified that error appears in the above-identified patent and that said Letters Patent is hereby corrected as shown below:

Col. 6, line 17, delete "and".

Claim 5, line 2, change "in" to --is--.

Signed and Sealed this

Twenty-seventh Day of December, 1988

Attest:

DONALD J. QUIGG

*Attesting Officer*    *Commissioner of Patents and Trademarks*